(12) United States Patent
Masuda et al.

(10) Patent No.: US 10,798,287 B2
(45) Date of Patent: Oct. 6, 2020

(54) ANALYSIS APPARATUS AND FOCUSING METHOD

(71) Applicant: ARKRAY, Inc., Kyoto-shi, Kyoto (JP)

(72) Inventors: Shigeki Masuda, Kyoto (JP); Kenji Nakanishi, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 25 days.

(21) Appl. No.: 16/025,103

(22) Filed: Jul. 2, 2018

(65) Prior Publication Data

US 2019/0020825 A1 Jan. 17, 2019

(30) Foreign Application Priority Data

Jul. 11, 2017 (JP) .................................. 2017-135299

(51) Int. Cl.
| | | |
|---|---|---|
| *H04N 5/232* | (2006.01) | |
| *G01N 15/14* | (2006.01) | |
| *G01N 33/493* | (2006.01) | |
| *G06T 7/00* | (2017.01) | |

(52) U.S. Cl.
CPC ... *H04N 5/232127* (2018.08); *G01N 15/1404* (2013.01); *G01N 15/147* (2013.01); *G01N 15/1434* (2013.01); *G01N 15/1484* (2013.01); *G01N 33/493* (2013.01); *G06T 7/0016* (2013.01); *H04N 5/23267* (2013.01); (Continued)

(58) Field of Classification Search
CPC ......... H04N 5/232127; H04N 5/23267; G01N 15/1404; G01N 15/147; G01N 15/1434; G01N 15/1484; G01N 33/493; G01N 2015/1413; G01N 2015/1452; G06T 7/0016; G06T 2207/30024
See application file for complete search history.

(56) References Cited

U.S. PATENT DOCUMENTS 6,476,398 B1 * 11/2002 Xu .......................... H01J 37/21
250/396 R
9,222,935 B1 * 12/2015 Bransky ............... G01N 33/521
(Continued)

FOREIGN PATENT DOCUMENTS

JP H10-104229 A 4/1998

OTHER PUBLICATIONS

The extended European search report issued by the European Patent Office on Nov. 8, 2018, which corresponds to EP18182960.7-1001 and is related to U.S. Appl. No. 16/025,103.

*Primary Examiner* — Maria E Vazquez Colon
(74) *Attorney, Agent, or Firm* — Studebaker & Brackett PC

(57) ABSTRACT

An analysis apparatus comprises a flow cell which has a flow passage for a liquid containing a tangible component; an image pickupper which picks up images of the liquid flowing through the flow passage; an adjuster which adjusts a relative position of the flow cell with respect to the image pickupper in relation to an optical axis direction of the image pickupper and a direction in which the liquid flows through the flow passage; and a controller which determines an image pickup position of the flow cell in at least one of the optical axis direction and the direction in which the liquid flows, on the basis of a number of pieces of the tangible component in focusing states existing in the images of the liquid picked up by the image pickupper at a plurality of positions at which the relative position differs.

10 Claims, 12 Drawing Sheets

(52) U.S. Cl.
CPC ................ *G01N 2015/1413* (2013.01); *G01N 2015/1452* (2013.01); *G06T 2207/30024* (2013.01)

(56) References Cited

U.S. PATENT DOCUMENTS

2002/0159060 A1* 10/2002 Roques .............. G01N 15/0227
356/335
2008/0311005 A1* 12/2008 Kim ................... G01N 15/1404
422/82.05

\* cited by examiner

CALCULATE NUMBER OF PIXELS
HAVING PIXEL VALUES OF
NOT LESS THAN THRESHOLD VALUE,
IN RELATION TO DIFFERENTIAL IMAGE
AT INSIDE OF MASK IMAGE
(INSIDE OF DOTTED LINE)

ANALYSIS APPARATUS AND FOCUSING METHOD

CROSS REFERENCE TO RELATED APPLICATIONS

This application claims priority to Japanese Patent Application No. 2017-135299 filed on Jul. 11, 2017 the entire contents of which are incorporated by reference herein.

TECHNICAL FIELD

The present disclosure relates to an analysis apparatus and a focusing method.

BACKGROUND ART

In relation to the inspection of collected urine, such a method is known that an image of a urine specimen is taken or picked up while allowing the specimen to flow through a flow cell, and the picked-up image is analyzed to thereby analyze sediment components contained in urine (tangible (solid) components contained in urine including, for example, blood cells, epithelial cells, casts, bacteria, and crystals) (see, for example, Patent Literature 1).

PRIOR ART LITERATURE

Patent Literature

Patent Literature 1: Japanese Patent Application Laid-Open No. 10-104229

SUMMARY

Technical Problem

If it is intended to take an image of the tangible component contained in the specimen flowing through the flow cell, it is considered that the autofocus control is performed on the basis of the contrast method which is one of the focusing methods. However, in the case of the contrast method, a problem arises such that the focusing accuracy is lowered if the contrast is low and if the object is relatively small with respect to the image pickup range. The sediment component contained in urine is the object which has a low contrast with respect to the urine liquid and which has a minute size. Therefore, the sediment component is a photographic subject which is unsuitable to use the contrast method.

An object of the present disclosure is to provide an apparatus and a method which make it possible to obtain an image of a tangible component contained in a specimen in which the focusing accuracy is high.

Solution to Problem

One aspect of the present disclosure resides in an analysis apparatus comprising a flow cell which includes a flow passage for a liquid containing a tangible component; an image pickupper configured to pick up images of the liquid flowing through the flow passage; an adjuster configured to adjust a relative position of the flow cell with respect to the image pickupper in relation to an optical axis direction of the image pickupper and a direction in which the liquid flows through the flow passage; and a controller configured to judge focusing states of pieces of the tangible component existing in the images of the liquid picked up by the image pickupper at a plurality of positions at which the relative position differs, such that the controller configured to determine an image pickup position of the flow cell in at least one of the optical axis direction and the direction in which the liquid flows, on the basis of a number of the pieces of the tangible component judged to be in the focusing states.

The analysis apparatus may further comprise a light source for image pickup which emits light a plurality of times within an exposure time for one time of exposure performed by the image pickupper.

Further, the controller can generate a cutout image which is an image including one piece of the tangible component and a background existing therearound included in the image picked up by the image pickupper, a blur image which is obtained by applying a blur process to the cutout image, a mask image which is obtained by applying a mask process to the background included in the cutout image, and a differential image which is based on differences between pixel values of the cutout image and pixel values of the blur image, and the controller can judge that the tangible component included in the cutout image is in the focusing state if a number of pixels each having a pixel value of not less than a threshold value existing in a range in which masking is not caused when the differential image is masked with the mask image is not less than a predetermined number.

Further, the controller can generate a cutout image which is an image including one piece of the tangible component and a background existing therearound included in the image picked up by the image pickupper, a blur image which is obtained by applying a blur process to the cutout image, a mask image which is obtained by applying a mask process to the background included in the cutout image, and a differential image which is based on differences between pixel values of the cutout image and pixel values of the blur image, and the controller can judge that the tangible component included in the cutout image is in the focusing state if a difference, which is provided between a standard deviation of pixel values of pixels existing in a range in which masking is not caused and a standard deviation of pixel values of pixels existing in a range in which masking is caused in relation to the differential image masked with the mask image, is not less than a threshold value.

Further, another aspect of the present disclosure includes the disclosure of a method corresponding to the analysis apparatus described above.

Advantageous Effect

According to the present disclosure, it is possible to obtain the image of the tangible component contained in a specimen in which the focusing accuracy is high.

DESCRIPTION OF THE EMBODIMENT

An explanation will be made below with reference to the drawings about a mode for carrying out the present disclosure. However, for example, the dimension or size, the material, the shape, and the relative arrangement of each of constitutive parts or components described in the embodiment are not intended to limit the scope of the disclosure only thereto unless specifically noted.

First Embodiment

Figure 1:
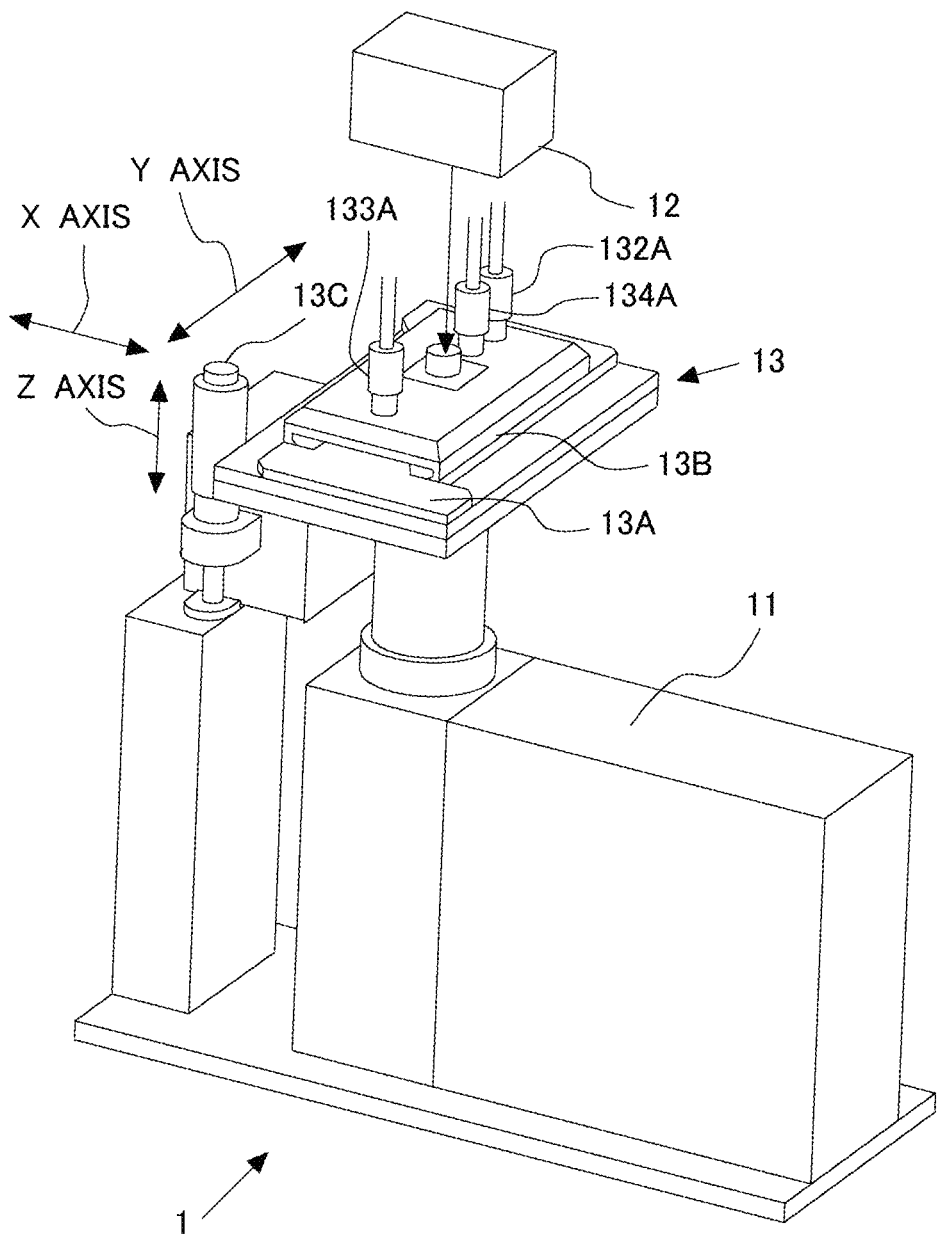
FIG. 1 shows a schematic structure of an image pickup apparatus according to an embodiment.

FIG. 1 shows a schematic structure of an image pickup apparatus 1 according to a first embodiment. The image pickup apparatus 1 is used for an analysis apparatus with which, for example, a tangible component contained in urine is analyzed by taking or picking up an image of, for example, urine as a specimen and analyzing the picked-up image. However, the image pickup apparatus 1 can be also applied to analyze any tangible component contained in a liquid specimen other than urine including, for example, body fluids and cells.

The image pickup apparatus 1 is provided with a camera 11 for picking up the image of the specimen, a light source 12 for image pickup, and a flow cell unit 13. The flow cell unit 13 is provided with a stage 13B on which a flow cell 13A for allowing the specimen to flow therethrough is fixed and arranged. The flow cell 13A may be detachable with respect to the stage 13B. Note that the length direction of the image pickup apparatus 1 shown in FIG. 1 is designated as the X axis direction in the orthogonal or rectangular coordinate system, the widthwise direction is designated as the Y axis direction, and the height direction is designated as the Z axis direction. The specimen flows in the Y axis direction in the flow cell 13A. A lens 11A described later on has an optical axis 11B which is arranged in the Z axis direction.

The flow cell unit 13 is provided with a focal point adjusting mechanism 13C which includes an actuator for relatively moving the flow cell 13A and the stage 13B on which the flow cell 13A is fixed and arranged with respect to the camera 11 in the Y axis direction and the Z axis direction. However, it is also allowable to adopt such a structure that no actuator is provided and the stage 13B is moved manually. Further, the focal point adjusting mechanism 13C may be provided with a mechanism for moving the camera 11 in place of the stage 13B. Alternatively, it is also allowable to adopt such a mechanism that both of the stage 13B and the camera 11 are moved. In short, it is enough that the focal point adjusting mechanism 13C is provided with such a mechanism that the relative position of the flow cell 13A with respect to the camera 11 can be changed by moving at least one of the camera 11 and the flow cell 13A in the Y axis direction and the Z axis direction.

Note that the camera 11 is an example of the "image pickupper". Further, the focal point adjusting mechanism 13C is an example of the "adjuster".

Figure 2:
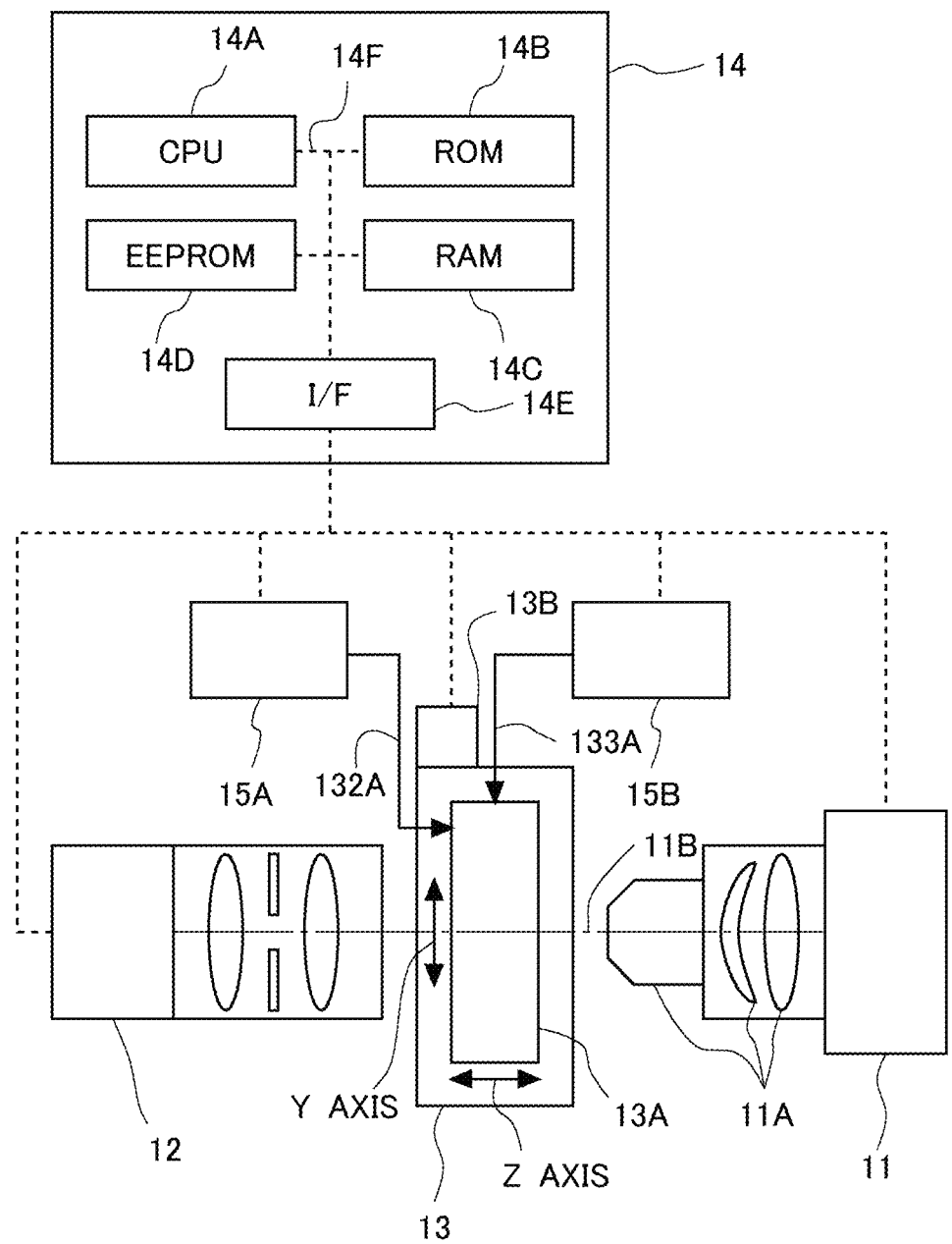
FIG. 2 shows a block diagram of the image pickup apparatus according to the embodiment.

FIG. 2 shows a block diagram of the image pickup apparatus 1 according to the first embodiment. The image pickup apparatus 1 is provided with a controller 14. The controller 14 includes CPU 14A, ROM 14B, RAM 14C, EEPROM 14D, and an interface circuit 14E which are mutually connected to one another by a bus line 14F.

CPU (central processing unit) 14A is operated on the basis of a program which is stored in ROM (read only memory) 14B and which is read to RAM (random access memory) 14C, and CPU 14A controls the entire image pickup apparatus 1. ROM 14B stores the program and data for operating CPU 14A. RAM 14C provides a work area for CPU 14A, and RAM 14C temporarily stores various data and the program. EEPROM 14D stores, for example, various setting data. The interface circuit 14E controls the communication between CPU 14A and various circuits.

The camera 11, the light source 12, the focal point adjusting mechanism 13C, and a first pump 15A and a second pump 15B are connected to the interface circuit 14E. These devices are controlled by the controller 14. The first pump 15A is a pump which supplies a sheath liquid to the flow cell 13A via a first supply tube 132A. The second pump 15B is a pump which supplies a specimen to the flow cell 13A via a second supply tube 133A. The sheath liquid is a liquid which controls the flow of the specimen in the flow cell 13A, to which physiological saline is applied, for example, when the specimen is urine. However, any solution other than physiological saline may be used as the sheath liquid.

The camera 11 includes the lens 11A which has an ocular lens and an objective lens. However, the lens 11A further includes an imaging lens in some cases. A static image (still image) of the tangible component contained in the specimen flowing through the flow cell 13A is picked up by the camera 11. The lighting period of the light source 12 depends on the flow rate of the specimen. The light source 12 is pulse-lighted, for example, at 0.5 to 10 μsec. The flashing timing of the light source 12 is determined while considering the relationship between the flow rate of the specimen and the lighting period of the light source 12. The light source 12 emits light a plurality of times for one time of exposure by pulse-lighting the light source 12 so that the number of pieces of the tangible component included in one image is increased. For example, a xenon lamp or a white LED can be adopted for the light source. However, there is no limitation thereto. It is also possible to adopt any other light source.

Further, in order to adjust the focus or focal point of the camera 11, a solution for the focal point adjustment test (hereinafter referred to as "test specimen") is allowed to flow together with the sheath liquid through the flow cell 13A, and the focal point adjusting mechanism 13C is adjusted so that the tangible component contained in the test specimen is in focus. Then, the focal point is fixed at the focusing point position, and a specimen as the analysis objective is thereafter allowed to flow together with the sheath liquid through the flow cell 13A so that the image pickup is carried out for the specimen.

Note that the image pickup is the magnifying image pickup. The lighting period of the light source 12 and the image pickup time (exposure time) of the camera 11 are synchronized by the controller 14. The adjustment of the focal point based on the use of the test specimen may be performed every time when a predetermined time elapses. Alternatively, the adjustment may be performed depending on the number of times of analysis of the specimen. Further alternatively, the adjustment may be performed every time when the specimen is analyzed, or every time when the image pickup apparatus 1 is started up. Further, the frequency of the execution of the focal point adjustment may be changed depending on the required accuracy of the focal point.

The test specimen contains the liquid and the tangible component. For example, a liquid, which contains a main component of PBS (phosphate buffer solution), is adopted as the liquid. An object, which has a size (for example, about 10 µm in diameter) approximate to the size of the tangible component of the actual specimen, is used as the tangible component of the test specimen. For example, human erythrocyte, or beads made of glass or resin can be applied as the object. The resin is, for example, PC (polycarbonate), PMMA (acrylic resin) or the like. However, an actual specimen (urine), which is prepared for the test, may be applied as the test specimen in some cases. The behavior of the test specimen (watershed control), which arises in the flow cell 13A in relation to a focusing point method explained below, also occurs when an actual specimen is used.

Next, an explanation will be made about the focusing point method executed by the controller 14. In this focusing point method, the focusing point position in the Y axis direction is detected, and then the focusing point position in the Z axis direction is detected. Accordingly, at first, the position, at which many pieces of the tangible component are found, is detected as the focusing point position in the Y axis direction.

Figure 3:
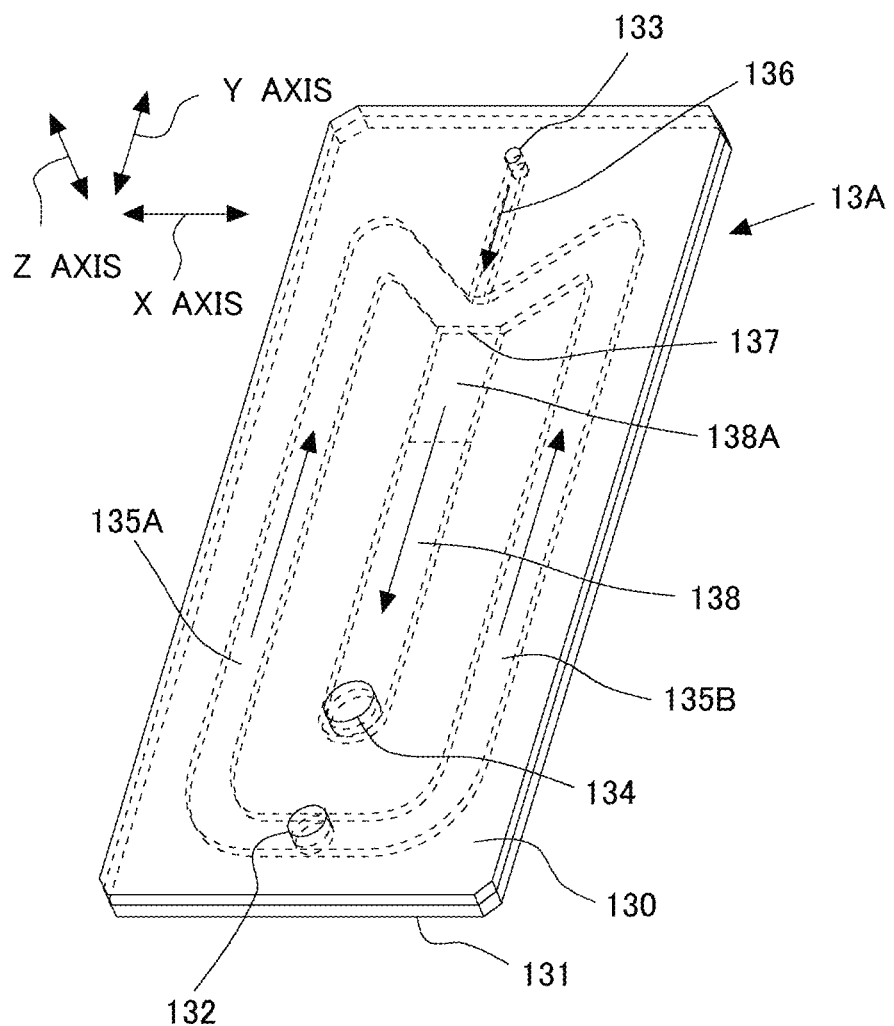
FIG. 3 shows a schematic structure of a flow cell.

FIG. 3 shows a schematic structure of the flow cell 13A. The flow cell 13A is formed by joining a first plate 130 and a second plate 131. As for the material for the flow cell 13A, it is possible to adopt a material which has a transparency for visible light of, for example, not less than 90%, such as PMMA (acrylic resin), COP (cycloolefin polymer), PDMS (polydimethylsiloxane), PP (polypropylene), and glass.

The first plate 130 is provided with a first supply port 132 for supplying the sheath liquid, a second supply port 133 for supplying the test specimen, and a discharge port 134 for discharging the sheath liquid and the test specimen. The first supply port 132 is provided on one end side in the longitudinal direction of the first plate 130. The second supply port 133 is provided on the other end side in the longitudinal direction of the first plate 130. The discharge port 134 is provided between the first supply port 132 and the second supply port 133 in the longitudinal direction of the first plate 130.

The first supply port 132, the second supply port 133, and the discharge port 134 are communicated with each other by passages 135A, 135B, 136, 138. Each of the passages 135A, 135B, 136, 138 is formed in a recessed form so that the cross section is rectangular from the surface disposed on the joined surface side of the first plate 130. Further, the cross section of each of the passages 135A, 135B, 136, 138 is formed so that the dimension in the widthwise direction (X axis direction as viewed in FIG. 1) is larger than the dimension in the depth direction (Z axis direction as viewed in FIG. 1).

The first passage 135A and the second passage 135B are connected to the first supply port 132. The first passage 135A and the second passage 135B are provided to cause the flows clockwise/counterclockwise respectively. The flows are directed toward the second supply port 133 along the outer edge of the first plate 130, and the flows merge at a merging portion 137. Further, the third passage 136 is connected to the second supply port 133. The third passage 136 merges with the first passage 135A and the second passage 135B at the merging portion 137. The merging portion 137 is connected to the discharge port 134 via the fourth passage 138. The fourth passage 138 is formed with a tapered portion 138A which is formed to have such a tapered shape that the depth of the fourth passage 138 (which is the length in the plate thickness direction of the first plate 130, along with the Z axis) is gradually decreased in the direction directed from the merging portion 137 to the discharge port 134.

Figure 4:
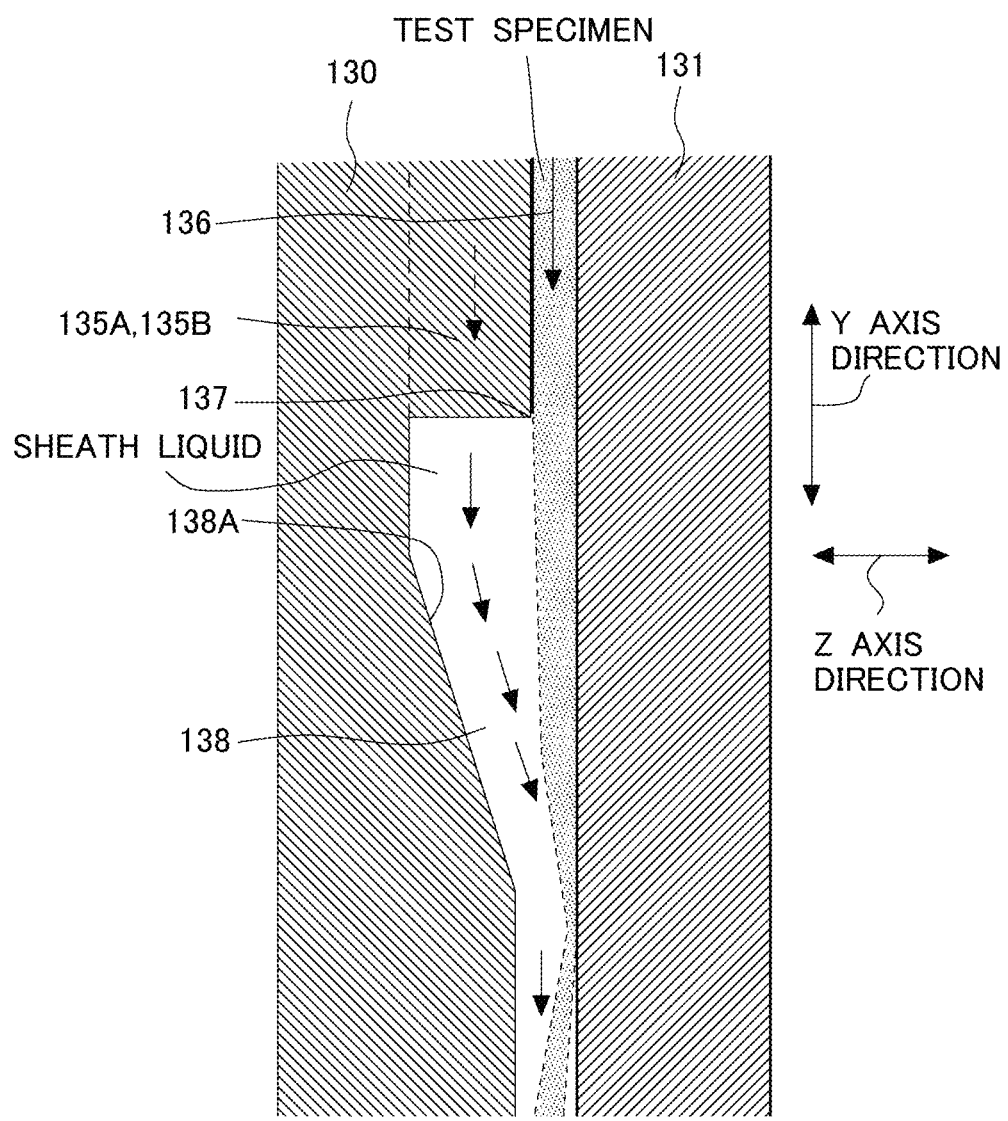
FIG. 4 shows a schematic structure of those disposed in the vicinity of a merging portion.

The first supply tube 132A shown in FIG. 1 is connected to the first supply port 132. The second supply tube 133A shown in FIG. 1 is connected to the second supply port 133. A discharge tube 134A shown in FIG. 1 is connected to the discharge port 134. The sheath liquid, which is supplied from the first supply tube 132A to the first supply port 132, flows through the first passage 135A and the second passage 135B. The test specimen, which is supplied from the second supply tube 133A to the second supply port 133, flows through the third passage 136. Then, the sheath liquid and the test specimen merge at the merging portion 137 to flow through the fourth passage 138. The sheath liquid and the test specimen are discharged from the discharge port 134 to the discharge tube 134A. FIG. 4 shows a schematic structure of those disposed in the vicinity of the merging portion 137. At the merging portion 137, the third passage 136 is arranged while being deviated toward the second plate 131. The test specimen flows along the second plate 131 at the merging portion 137.

Figure 5:
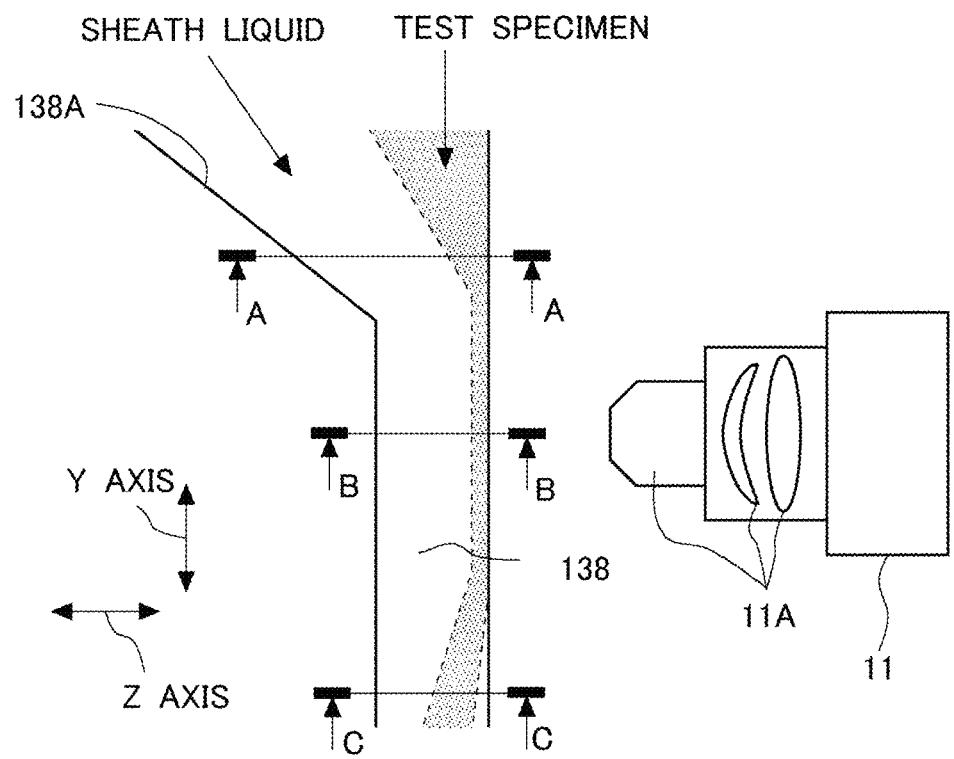
FIG. 5 shows a distribution of a sheath liquid and a test specimen flowing through the flow cell.
Figure 5:
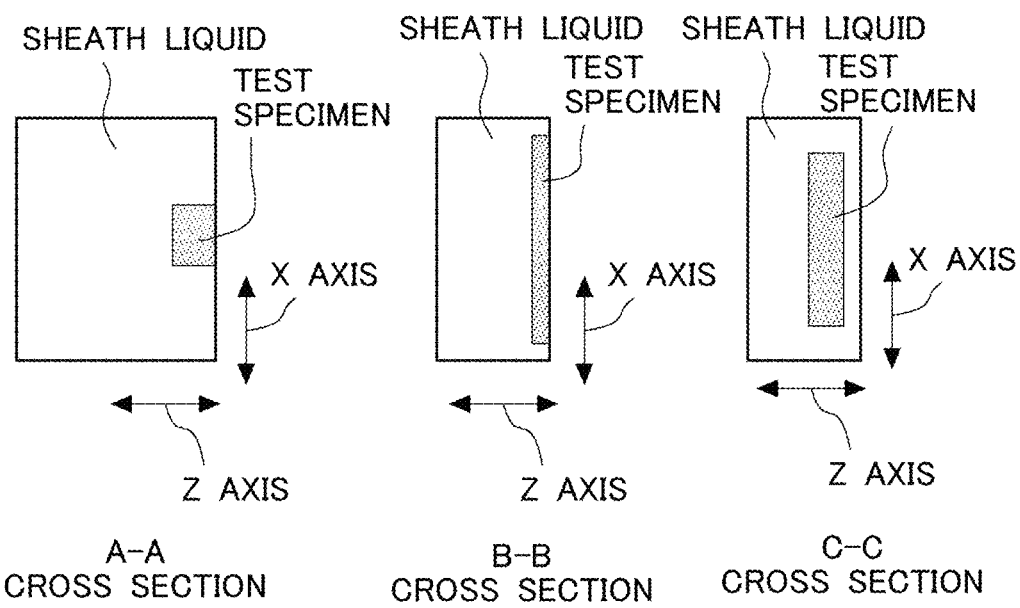

FIG. 5 shows a distribution of the sheath liquid and the test specimen flowing through the fourth passage 138. The sheath liquid and the test specimen are supplied separately from the upper side as viewed in FIG. 5, and then the sheath liquid and the test specimen merge at the merging portion 137. The test specimen in the sheath liquid is concentrated in a relatively narrow range disposed on the wall surface side of the second plate 131 immediately after the sheath liquid and the test specimen merge at the merging portion 137 (see A-A cross section shown in FIG. 5). After that, when the test specimen flows along the tapered portion 138A, then the test specimen is pushed by the sheath liquid, and the test specimen is spread in a flat form along the wall surface in the vicinity of the wall surface of the second plate 131 (see B-B cross section shown in FIG. 5). When the test specimen further flows, then the test specimen is separated from the wall surface of the second plate 131 in accordance with the Tubular-pinch effect, and the test specimen is lifted toward the central direction of the fourth passage 138 (see C-C cross section shown in FIG. 5).

For example, if the environment changes, if the fixed states of the respective members change, and/or if the balance of the respective members collapses, then the distribution of the test specimen changes in the flow cell 13A in some cases, and/or the uniformity of the flow of the test specimen lowers in other cases. The distribution of the tangible component is affected by the distribution of the test specimen. When the image is picked up, it is possible to raise the analysis accuracy of the tangible component by picking up the image at the position at which images of a larger number of pieces of the tangible component can be picked up. In the flow cell 13A, as shown in the cross-sectional view shown in FIG. 5, the flow of the test specimen changes depending on the position in the Y axis direction. The width of the specimen is increased in the Z axis direction at the position of the C-C cross section shown in FIG. 5 as compared with the position of the B-B cross section. The tangible component in the test specimen is distributed while being spread in the Z axis direction at the position of the C-C cross section shown in FIG. 5, and hence this position is not suitable for photographing the image of the tangible component. On the other hand, at the position of the B-B cross section shown in FIG. 5, the sheath liquid flows so that the test specimen is pressed against the second plate 131 from the upper position. The test specimen is squashed by the sheath liquid, and the test specimen is spread in a thin form. On this account, at the position of the B-B cross section shown in FIG. 5, the tangible component in the test specimen exists while being not spread in the Z axis direction. It is easy to adjust the focus or focal point. The image pickup position of the camera 11 can be adjusted to the position of the B-B cross section by moving the flow cell 13A in the Y axis direction.

The flow cell 13A is moved in the Y axis direction a plurality of times. The images are picked up at respective positions by means of the camera 11. The picked-up images are analyzed, and the numbers of pieces of the tangible component being in focus are determined at the respective positions. Then, the position, at which the image having the largest number of pieces of the tangible component being in focus is picked up, is detected as the focusing point position in the Y axis direction.

Specifically, the focal point adjusting mechanism 13C has the stage 13B for fixing and arranging the flow cell 13A to repeat the action in which the stage 13B is moved at a predetermined pitch in the Y axis direction and the image is picked up every time when the stage 13B is moved. The pitch is, for example, 5 μm. As for the distance of movement, the movement is performed, for example, by ±20 μm from the movement start position. Then, the numbers of pieces of the tangible component being in focus at the respective positions (hereinafter referred to as "focusing point number" as well) are calculated, and the position, which has the largest focusing point number, is designated as the focusing point position in the Y axis direction.

Subsequently, the position, at which a large number of pieces of the tangible component are found in the Z axis direction, is detected as the focusing point position. The Z axis direction is the direction of the optical axis 11B of the objective lens included in the camera 11. The focal point position of the objective lens is deviated in the direction of the optical axis 11B by relatively moving the flow cell 13A in the Z axis direction with respect to the camera 11. Thus, the position, at which a large number of pieces of the tangible component are found within a range of the depth of field, is detected. If a larger number of pieces of the tangible component exist within the range of the depth of field of the objective lens, the analysis accuracy of the tangible component is raised.

Specifically, the stage 13B is moved at a predetermined pitch in the Z axis direction from the focusing point position in the Y axis direction, and the image is picked up every time when the movement is performed. In this procedure, the pitch is, for example, 5 μm as well. The range of movement is, for example, ±20 μm from the movement start position (focusing point position in the Y axis direction) as well. Then, the focusing point numbers are calculated at the respective positions, and the position, which has the largest focusing point number, is designated as the focusing point position in the Z axis direction. The focusing point position, which is determined for the both axes in the Y axis direction and the Z axis direction, is fixed as the image pickup position for the specimen. Note that in the foregoing explanation, the focusing point position in the Y axis direction is determined earlier, and then the focusing point position in the Z axis direction is determined. However, in place thereof, it is also allowable that the focusing point position in the Z axis direction is determined earlier, and then the focusing point position in the Y axis direction is determined.

The pitch, which is provided when the flow cell unit 13 is moved, is, for example, 5 μm. The pitch is previously set as the pitch which is required to determine the focusing point position in the concerning direction at a desired accuracy. Further, the range of movement is, for example, ±20 μm. The movement range is previously set as the movement range which is required to determine the focusing point position in the concerning direction at a desired accuracy.

Note that the detection accuracy of the focusing point position can be raised by narrowing the pitch or increasing the movement range. However, it is feared that a long time may be required, because it is necessary to perform the image pickup and the calculation to a greater extent. On the other hand, the time, which is required for the image pickup and the calculation, can be shortened or reduced by widening the pitch or decreasing the movement range. However, it is feared that the detection accuracy of the focusing point position may be lowered. On this account, the pitch and the movement range, which are provided when the movement is performed, may be determined depending on the selection and the degree of precedence of the time required for the image pickup and the calculation and the required detection accuracy. Further, the pitch in the Y axis direction may be determined, for example, by means of any experiment or simulation. The pitch in the Z axis direction may be set depending on the depth of field.

Next, an explanation will be made about a method for image processing and image analysis used to determine the focusing point position described above. In order to perform the image processing and the analysis, CPU 14A executes the following five steps by executing the program.

1. Image pickup: A predetermined number (for example, 100 to 500 shots) of images are picked up by using the camera 11 at respective positions at which the movement is performed at a predetermined pitch in the Y axis direction or the Z axis direction. Note that an identical number of images are picked up at the respective positions. Data of the respective pickup images is stored, for example, in RAM 14C.

2. Preparation of background image: CPU 14A prepares the background image by averaging pixel values of respective pixels for each of the pickup images by using the data of the pickup images having been stored. The pixel value may be either the luminance of each of the pixels or the RGB value.

3. Cutout process: CPU 14A compares the background image with the picked-up image. The image, which has a difference and which has a size of, for example, about 10 μm, is cut out, and the image is stored in RAM 14C. Note that in the foregoing explanation, for example, the image of about 10 μm is cut out. This is because the size of the tangible component contained in the test specimen is, for example, about 10 μm. Therefore, the size of the image to be cut out may be set depending on the size of the tangible component.

4. Focused focal point judging process: CPU 14A classifies the cutout images stored in RAM 14C into the focusing point images which are the images that are in focus and the non-focusing point images which are the images that are not in focus.

5. Detection of focusing point position: CPU 14A counts the number of the focusing point images at each of the positions to determine the number of the focusing points. The number of the focusing points is compared with those of the other positions in relation to each of the axes. The position, at which the number of the focusing points is maximized, is designated as the focusing point position in relation to the concerning axis.

Figure 6:
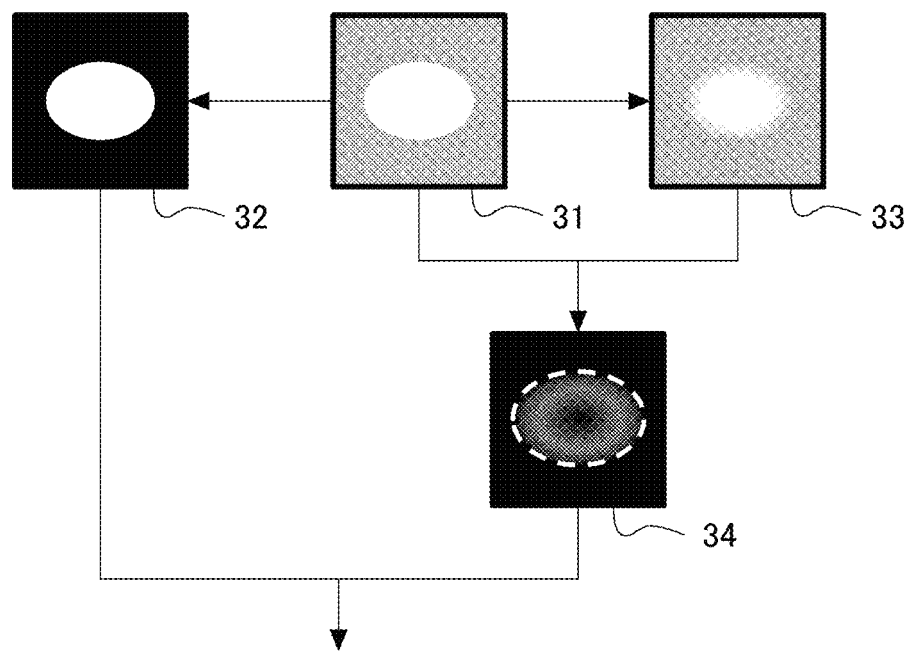
FIG. 6 explains a focusing point judging process.

An explanation will be made about details of the focusing point judging process described above. FIG. 6 explains the focusing point judging process. The focusing point judging process is performed by CPU 14A. A cutout image 31 is the image which is cut out by the cutout process. The cutout image 31 corresponds to the image which is obtained such that one piece of the tangible component included in the picked-up image is surrounded by a rectangle and the interior thereof is cut out.

Subsequently, a mask image 32 is prepared from the cutout image 31. Any arbitrary method, which includes, for example, the discrimination analysis method and the Canny filter, can be used to prepare the mask image 32. The mask image 32 corresponds to the image which is obtained by masking the background (area other than the tangible component) included in the cutout image 31. On the other hand, a blur (Blur) image 33, which is provided for the cutout image 31, is prepared. Any arbitrary method, which includes, for example, the Gaussian filter, can be used to prepare the blur image 33. The blur image 33 is the image in which the edge portion of the photographic subject is blurred. The blur image 33 corresponds to the image in which the boundary between the tangible component and the background is blurred.

Subsequently, a differential image 34 between the blur image 33 and the cutout image 31 is prepared. The differential image 34 is the image which is obtained by determining the differences in the pixel values of the corresponding pixels between the blur image 33 and the cutout image 31. In this context, in the case of the image which is in focus, the number of pixels in which the differences in the pixel value are relatively large is increased. That is, in the case of the image which is not in focus, the boundary between the tangible component and the background is originally blurred. Therefore, the difference in the pixel value is small between the cutout image 31 and the blur image 33.

Subsequently, the pixels, in which the pixel values are not less than a threshold value, are counted, provided that the pixels exist within a range (range disposed at the inside of the dotted line shown in FIG. 6) in which masking is not caused when the differential image 34 is masked with the mask image 32. The threshold value is the lower limit value of the pixel value at which the image is in focus, and the threshold value is previously determined. If the number of the pixels counted as described above is not less than a threshold value, it is judged that the image is the focusing point image. The threshold value referred to herein is the lower limit value of the pixel value at which the focusing point is assumed.

Figure 7:
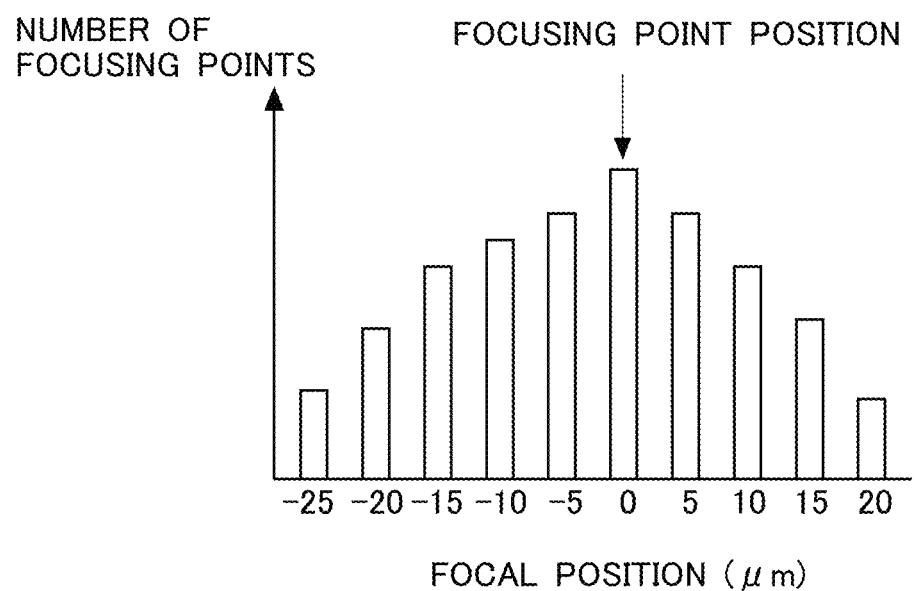
FIG. 7 shows a relationship between a focal position and a number of focusing points.

The number of the focusing point images, i.e., the focusing point number (number of focusing points) is counted for all of the picked-up images at the respective positions at which the movement is performed at the predetermined pitch in the Y axis direction and the Z axis direction. The number is compared with the focusing point numbers at other positions. FIG. 7 shows a relationship between the focal position and the number of focusing points. For example, such a histogram is prepared, and the focal position, which has the largest number of focusing points, is detected as the focusing point position. Note that FIG. 7 also includes a measurement result of the number of focusing points obtained when the movement is performed by −25 μm, unlike the explanation about the movement range described above (±20 μm).

In the histogram as shown in FIG. 7, if the maximum value of the number of focusing points is not located at the both ends of the movement range (i.e., −25 μm and 20 μm shown in FIG. 7), it is considered that the focal point position, at which the number of focusing points has the maximum value, is the focusing point position. However, if the maximum value of the number of focusing points is located at the both ends of the movement range (i.e., −25 μm and 20 μm shown in FIG. 7), there is also such a possibility that the focal position, at which the number of focusing points has the maximum value, may exist at the outside of the movement range. In such a situation, it is also allowable that the movement range value may be further widened to detect the focal position at which the number of focusing points has the maximum value.

Further, the position, at which the focusing point number has the maximum value, is designated as the focusing point position. However, the position, at which the focusing point number has the maximum value, exists in some cases at any position through which the apparatus passes during the movement, depending on the pitch for the movement. Therefore, a relational expression between the focal position and the focusing point number may be determined from the histogram shown in FIG. 7. The position, at which the focusing point number is maximized, may be determined by using this expression.

Figure 8:
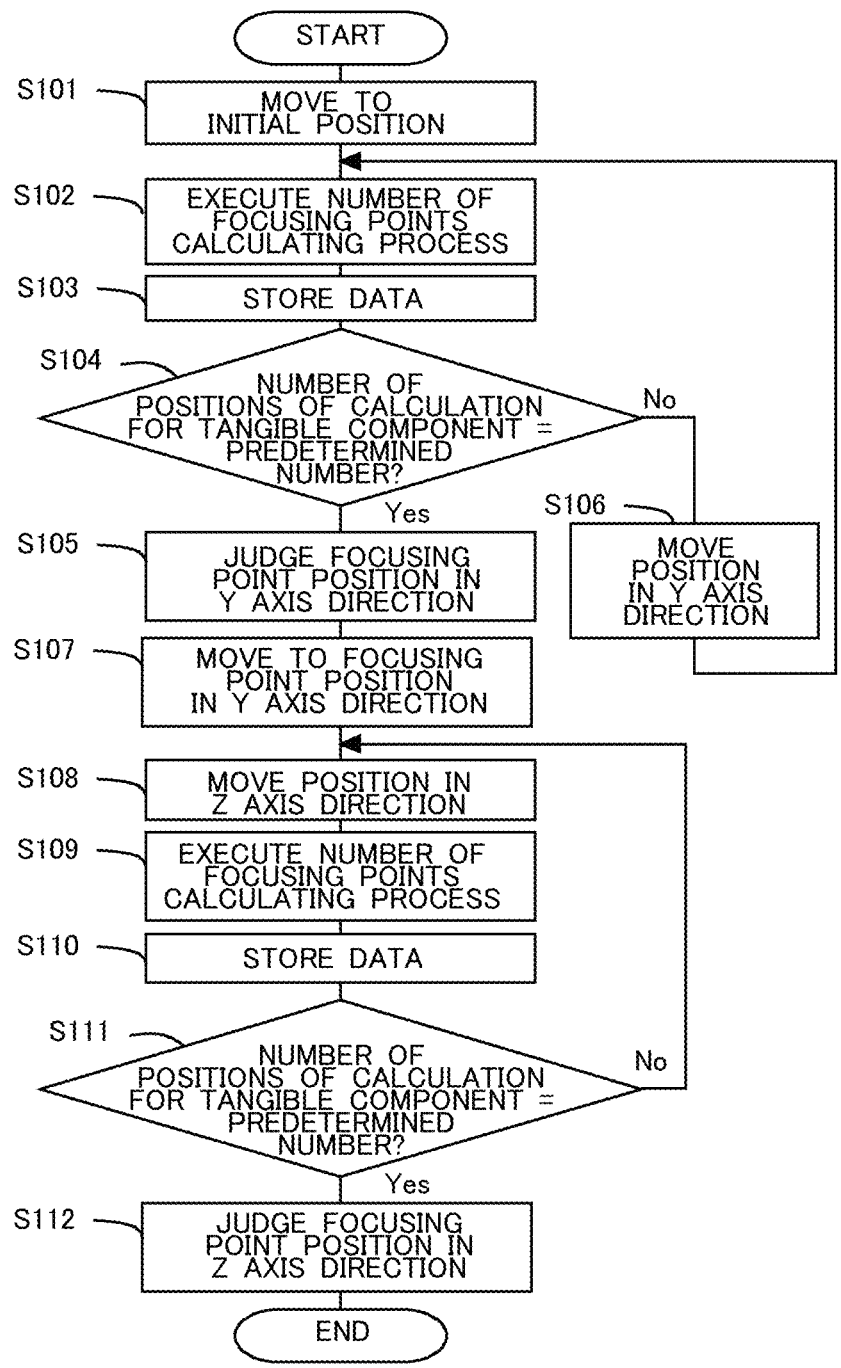
FIG. 8 shows a flow chart illustrating a flow to determine the focusing point position.

FIG. 8 shows a flow chart illustrating a flow to determine the focusing point position. This flow chart is executed in accordance with the program executed by CPU 14A of the controller 14 if it is necessary to determine the focusing point position. In the first embodiment, the controller 14 operates as the controller for detecting the focusing point position.

In Step S101, CPU 14A controls the focal point adjusting mechanism 13C so that the flow cell 13A, which is fixed and arranged on the stage 13B of the flow cell unit 13, is moved to the initial position. As for the initial position, the optimum position is previously determined by means of any experiment or the like or by means of any simulation or the like within a range in which the focusing point position may be provided. Alternatively, the focusing point position, which has been determined last time, may be set as the initial position provided this time. If the process of Step S101 is terminated, the routine proceeds to Step S102.

In Step S102, CPU 14A uses the pickup images (stored in RAM 14C) obtained at the respective positions in the Y axis direction. CPU 14A executes the number of focusing points calculating process to calculate the focusing point number. This will be described later on. Then, if the process of Step S102 is terminated, the routine proceeds to Step S103. CPU 14A stores the focusing point number in RAM 14C while correlating the focusing point number with the position in the Y axis direction. If the process of Step S103 is terminated, the routine proceeds to Step S104.

In Step S104, CPU 14A judges whether or not the number of positions (number of times) at which the focusing point number is calculated in the Y axis direction arrives at a predetermined number (for example, 9 to 10). The predetermined number is determined depending on the pitch described above and the movement range. If the affirmative judgment is made in Step S104, the routine proceeds to Step S105. On the other hand, if the negative judgment is made, the routine proceeds to Step S106.

In Step S106, CPU 14A controls the focal point adjusting mechanism 13C so that the position in the Y axis direction of the flow cell 13A is moved at a predetermined pitch (for example, 5 μm). If the process of Step S106 is terminated, the routine returns to Step S102. That is, the position in the Y axis direction of the flow cell 13A is moved by the focal point adjusting mechanism 13C until the number of positions, at which the focusing point number is calculated for the Y axis direction, arrives at the predetermined number. The number of focusing points calculating process is carried out at the respective positions.

On the other hand, in Step S105, CPU 14A judges the focusing point position in the Y axis direction. That is, CPU 14A performs the image processing and the image analysis described above by using the pickup images at the respective positions stored in RAM 14C. It is judged that the position, at which the number is the largest of the focusing point numbers at the respective positions, is the focusing point position in the Y axis direction. If the process of Step S105 is terminated, the routine proceeds to Step S107.

In Step S107, CPU 14A controls the focal point adjusting mechanism 13C so that the flow cell 13A is moved to the focusing point position in the Y axis direction. If the process of Step S107 is terminated, the routine proceeds to Step S108. CPU 14A controls the focal point adjusting mechanism 13C so that the flow cell 13A is moved at a predetermined pitch (for example, 5 μm) in the Z axis direction. If the process of Step S108 is terminated, the routine proceeds to Step S109.

In Step S109, CPU 14A uses the pickup images (stored in RAM 14C) obtained at the respective positions in the Z axis direction. CPU 14A executes the number of focusing points calculating process to calculate the focusing point number. The method of the number of focusing points calculating process itself is the same as that of the process for the image picked up in the Y axis direction. If the process of Step S109 is terminated, the routine proceeds to Step S110. CPU 14A stores the focusing point number in RAM 14C while correlating the focusing point number with the position in the Z axis direction. If the process of Step S110 is terminated, the routine proceeds to Step S111.

In Step S111, CPU 14A judges whether or not the number of positions (number of times) at which the focusing point number is calculated in the Z axis direction arrives at a predetermined number (for example, 9 to 10). The predetermined number is determined depending on the pitch described above and the movement range. If the affirmative judgment is made in Step S111, the routine proceeds to Step S112. On the other hand, if the negative judgment is made, the routine proceeds to Step S108. That is, the position in the Z axis direction of the flow cell unit 13 is moved by the focal point adjusting mechanism 13C until the number of positions, at which the focusing point number is calculated for the Z axis direction, arrives at the predetermined number. The number of focusing points calculating process is carried out at the respective positions.

In Step S112, CPU 14A judges the focusing point position in the Z axis direction. That is, it is judged that the position, at which the number is the largest of the focusing point numbers at the respective positions stored in RAM 14C, is the focusing point position in the Z axis direction. If the process of Step S112 is terminated, this flow chart is terminated. The focusing point position in the Z axis direction determined as described above is also the focusing point position in the Y axis direction. Therefore, the focusing point position is the final focusing point position at which the image is in focus in relation to the both axes.

Figure 9:
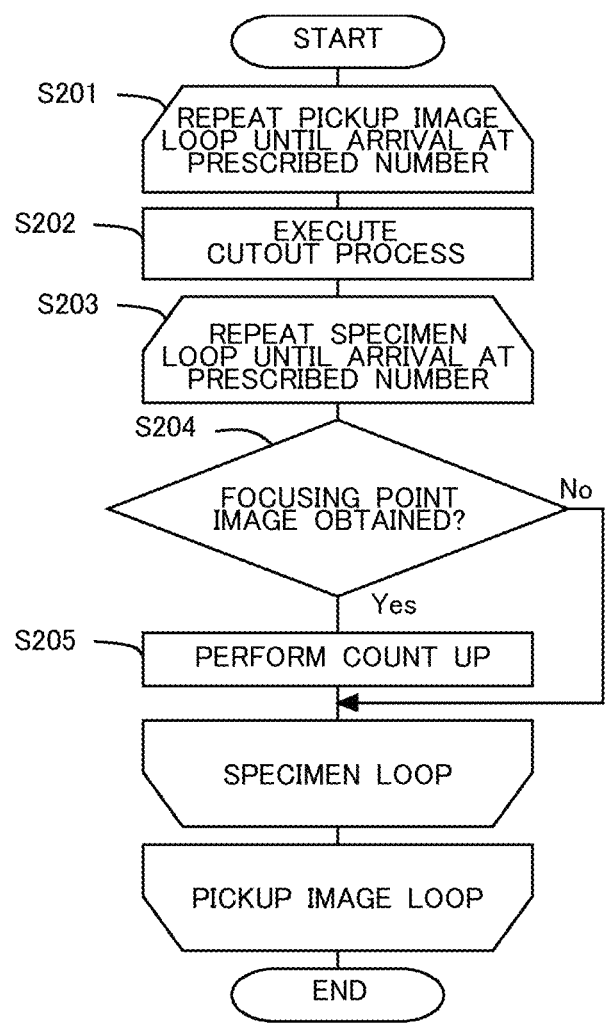
FIG. 9 shows a flow chart illustrating a flow of a number of focusing points calculating process.

Next, an explanation will be made about the number of focusing points calculating process executed in Step S102 and Step S109. FIG. 9 shows a flow chart illustrating a flow of the number of focusing points calculating process. This flow chart is executed by CPU 14A of the controller 14 by executing the program in Step S102 and Step S109 of the flow chart shown in FIG. 8.

In Step S201, CPU 14A executes a pickup image loop. The pickup image loop is repeated until the number of pickup images arrives at a prescribed number (for example, 100 to 500 shots). In Step S202, a cutout process is carried out.

In Step S203, CPU 14A executes a specimen loop. The specimen loop is repeated until the number of cutout pieces of the tangible component arrives at a prescribed number. The prescribed number referred to herein is previously set as a number of cutout pieces required to determine the focusing point position at a desired accuracy. The prescribed number is, for example, 2000 to 3000. However, the prescribed number may be a number which corresponds to all pieces of the tangible component contained in the picked-up image.

In Step S204, CPU 14A judges whether or not the objective cutout image is a focusing point image. That is, CPU 14A performs a focusing point judging process. This will be described later on. If the affirmative judgment is made in Step S204, the routine proceeds to Step S205. CPU 14A counts up the number of focusing points. After that, the specimen loop is repeated. On the other hand, if the negative judgment is made in Step S204, the specimen loop is repeated as it is.

In this way, CPU 14A counts the number of focusing points of each of the picked-up images until arrival at the number of pickup images at each of the focal point positions.

Figure 10:
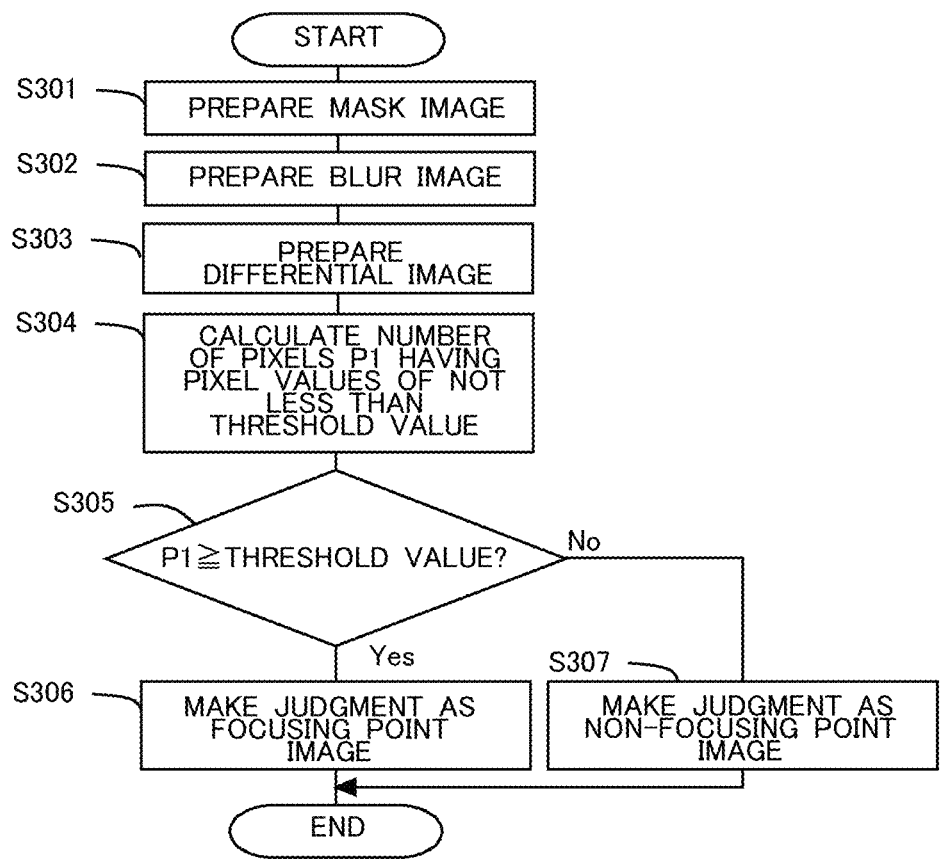
FIG. 10 shows a flow chart illustrating a flow of the focusing point judging process according to the first embodiment.

Next, the focusing point judging process will be explained. FIG. 10 shows a flow chart illustrating a flow of the focusing point judging process according to the first embodiment. This flow chart is executed by CPU 14A of the controller 14 by executing the program in Step S204 of the flow chart shown in FIG. 9.

CPU 14A prepares the mask image 32 in Step S301, CPU 14A prepares the blur image 33 in Step S302, and CPU 14A prepares the differential image 34 in Step S303. Then, in Step S304, CPU 14A calculates the number of pixels P1 having pixel values of not less than the threshold value existing in the range (range disposed at the inside of the dotted line shown in FIG. 6) not masked when the differential image 34 is masked with the mask image 32.

Subsequently, in Step S305, CPU 14A judges whether or not the number of pixels P1 calculated in Step S304 is not less than a threshold value. If the affirmative judgment is made in Step S305, then the routine proceeds to Step S306, and CPU 14A judges that the image is the focusing point image (to be in the focusing state). On the other hand, if the negative judgment is made, then the routine proceeds to Step S307, and CPU 14A judges that the image is the non-focusing point image (not to be in the focusing state).

As explained above, according to the first embodiment, according to the first embodiment, it is possible to raise the focusing point accuracy for the image which has a low contrast and which includes the object that is relatively small with respect to the image pickup range. That is, it is possible to obtain the pickup image having the preferred focusing accuracy for the urine specimen for which any preferred focusing accuracy is not obtained by the contrast method.

Second Embodiment

In the second embodiment, the focusing point judging process differs from the process of the first embodiment. The other features of the apparatus, the control and the like are the same as those of the first embodiment, any explanation of which will be omitted. In this context, in the case of the focusing point judging process described in the first embodiment, the process is simple and the calculation speed is quickened. However, the robustness is low with respect to any image having a low signal-to-noise ratio. On this account, in the second embodiment, the robustness is improved by comparing the inside and the outside of the mask image.

Figure 11:
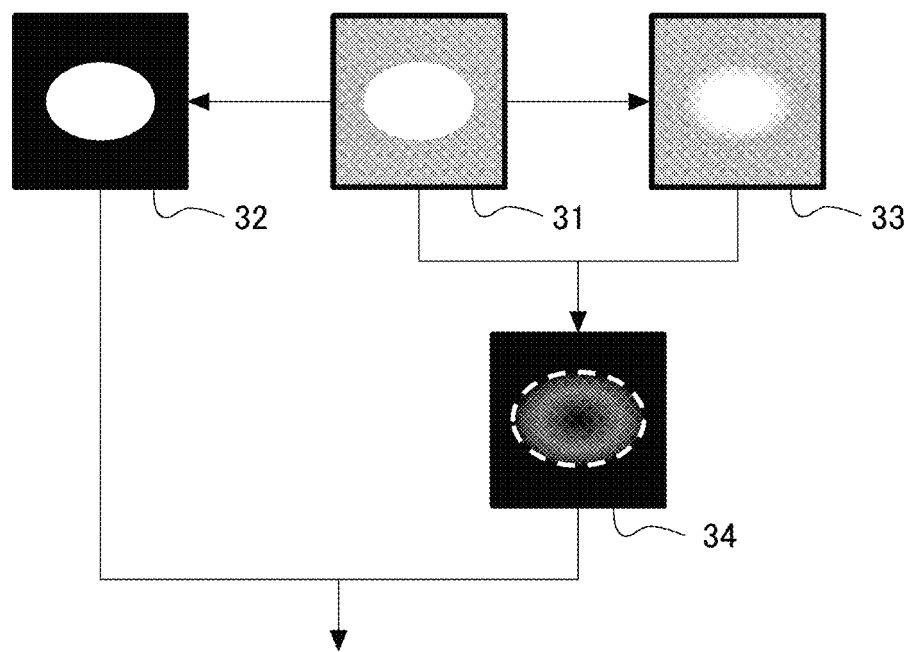
FIG. 11 explains a focusing point judging process.

FIG. 11 explains the focusing point judging process. The preparation of the mask image 32, the preparation of the blur image 33, and the preparation of the differential image 34 are the same as those of the first embodiment. Note that in the following description, the range, which corresponds to the masked range (black colored range) of the mask image 32 shown in FIG. 11, is referred to as "outside of the mask image", and the range, which corresponds to the unmasked range (white colored range) of the mask image 32 shown in FIG. 11, is referred to as "inside of the mask image".

In the focusing point state, a portion exists in the mask image, in which the difference in the pixel value is large between the cutout image 31 and the mask image 32. Therefore, the standard deviation of the pixel values is increased for the differential image 34 existing inside the mask image (range disposed at the inside of the dotted line shown in FIG. 11). On the other hand, the standard deviation of the pixel values is small for the differential image 34 existing outside the mask image (range disposed at the outside of the dotted line shown in FIG. 11). On this account, there is such a tendency that the difference, which is provided between the standard deviation of the pixel values of the differential image 34 disposed at the inside of the mask image and the standard deviation of the pixel values of the differential image 34 disposed at the outside of the mask image, is increased, provided that the image is in focus.

Therefore, the difference, which is provided between the standard deviation of the pixel values of the differential image 34 disposed at the inside of the mask image and the standard deviation of the pixel values of the differential image 34 disposed at the outside of the mask image, is calculated. If the difference is not less than a threshold value, it is possible to judge that the image is the focusing point image. This threshold value is the lower limit value of the difference in the standard deviation at which the image is in focus. The threshold value is previously set. In this way, the focusing point accuracy is further improved by using the data of the outside of the mask image as well.

Figure 12:
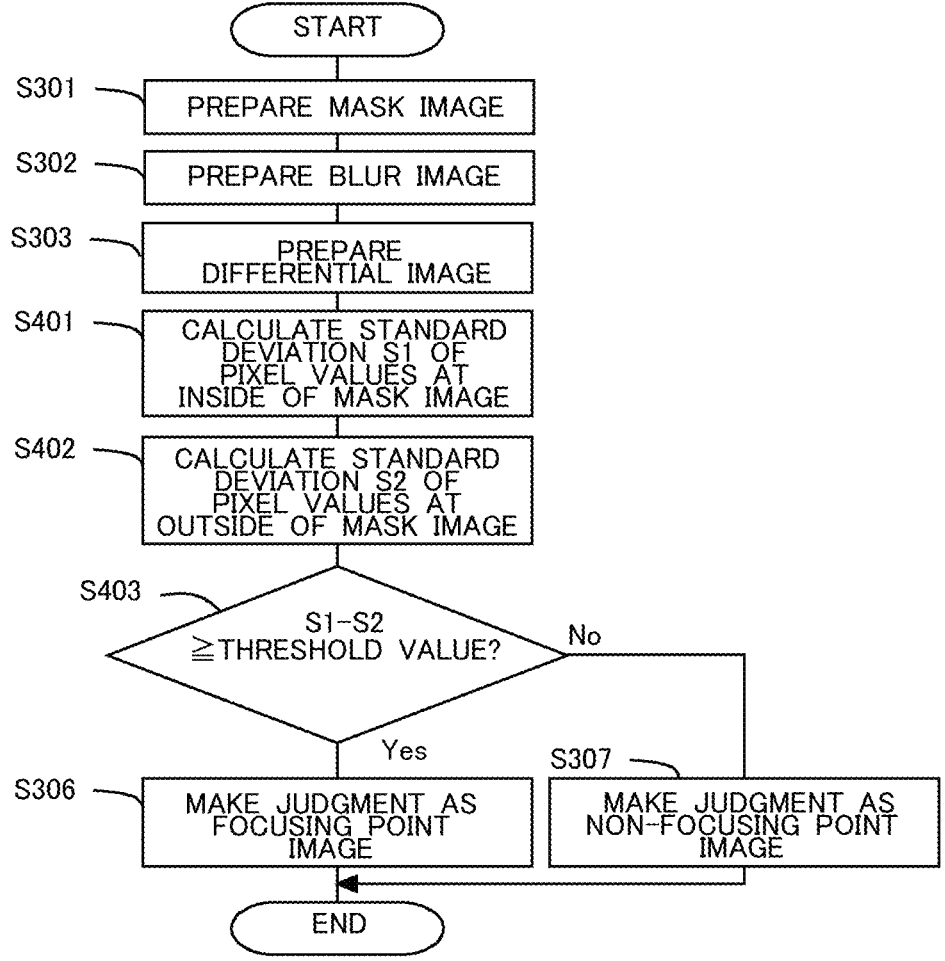
FIG. 12 shows a flow chart illustrating a flow of the focusing point judging process according to a second embodiment.

FIG. 12 shows a flow chart illustrating a flow of the focusing point judging process according to a second embodiment. This flow chart is executed by CPU 14A of the controller 14 by executing the program in Step S204 of the flow chart shown in FIG. 9. Note that the steps, in which the same processes as those of FIG. 10 are performed, are designated by the same reference numerals, any explanation of which is omitted.

In the flow chart shown in FIG. 12, if the process of Step S303 is terminated, the routine proceeds to Step S401. CPU 14A calculates the standard deviation S1 of the pixel values of the differential image 34 disposed at the inside of the mask image. If the process of Step S401 is terminated, the routine proceeds to Step S402. CPU 14A calculates the standard deviation S2 of the pixel values of the differential image 34 disposed at the outside of the mask image.

If the process of Step S402 is terminated, the routine proceeds to Step S403. CPU 14A judges whether or not the difference, which is provided between the standard deviation S1 of the pixel values of the differential image 34 disposed at the inside of the mask image and the standard deviation S2 of the pixel values of the differential image 34 disposed at the outside of the mask image, is not less than a threshold value. The threshold value referred to herein is the lower limit value of the value which indicates that the difference between the standard deviation S1 of the pixel values of the differential image 34 disposed at the inside of the mask image and the standard deviation S2 of the pixel values of the differential image 34 disposed at the outside of the mask image resides in the focusing point. The threshold value is determined beforehand by means of, for example, any experiment or any simulation.

If the affirmative judgment is made in Step S403, then the routine proceeds to Step S306, and CPU 14A judges that the image is the focusing point image. On the other hand, if the negative judgment is made, then the routine proceeds to Step S307, and CPU 14A judges that the image is the non-focusing point image.

In this way, it is possible to raise the robustness with respect to the image having a low signal-to-noise ratio by performing the judgment by using the data of those disposed at the outside of the mask image. Therefore, it is possible to raise the focusing point accuracy.

In the embodiment described above, the image pickup position is adjusted in relation to the two directions of the direction in which the liquid flows through the flow cell 13A and the direction of the optical axis 11B. However, it is also allowable that the image pickup position is adjusted in relation to only any one of the directions. Note that the embodiment described above has been explained as exemplified by the example of the mode in which the test specimen is brought in contact with the wall surface of the flow cell 13A after the test specimen passes through the tapered portion 138A of the flow cell 13A. However, the structure of the flow cell and the flow of the test specimen are not limited to only those explained in this mode. For example, it is also allowable to use a flow cell having such a structure that the sheath liquid surrounds the test specimen after the passage through the tapered portion 138A of the flow cell 13A, and the test specimen is stretched to be thin at the central portion of the sheath liquid. In this case, the sheath liquid intervenes between the camera and the test specimen. However, even in such a situation, it is possible to accurately adjust the focus.

The invention claimed is:
1. An analysis apparatus comprising:
   a flow cell which includes a flow passage for a liquid containing a tangible component;
   a camera configured to pick up images of the liquid flowing through the flow passage;
   an adjuster configured to adjust a relative position of the flow cell with respect to the camera in relation to an optical axis direction of the camera and/or a direction in which the liquid flows through the flow passage; and
   a controller configured to judge focusing states of pieces of the tangible component in a cutout image obtained by cutting out an image including the tangible component from a plurality of images of the liquid picked up by the camera at a plurality of positions at which the relative position differs, such that the controller is configured to determine an image pickup position of the flow cell in at least one of the optical axis direction and the direction in which the liquid flows, on the basis of a number of the pieces of the tangible component judged to be in the focusing states, wherein the controller is further configured to generate the cutout image which is an image including one piece of the tangible component and a background existing therearound included in the image picked up by the camera, a blur image which is obtained by applying a blur process to the cutout image, a mask image which is obtained by applying a mask process to the background included in the cutout image, and a differential image which is based on differences between pixel values of the cutout image and pixel values of the blur image, and the controller is further configured to judge that the tangible component included in the cutout image is in the focusing state if a number of pixels each having a pixel value of not less than a threshold value existing in a range in which masking is not caused when the differential image is masked with the mask image is not less than a predetermined number.

2. The analysis apparatus according to claim 1, further comprising a light source for image pickup which emits light a plurality of times within an exposure time for one time of exposure performed by the camera.

3. The analysis apparatus according to claim 1, wherein
the flow passage includes a merging portion where a passage through which the test specimen containing the tangible component flows and a passage through which a sheath liquid flows merge, and a tapered portion formed downstream of the merging portion;
the test specimen and the sheath liquid which flowed through the tapered portion flow through the flow passage in a laminar flow without being mixed; and
the camera picks up images of the liquid flowing downstream from the tapered portion.

4. An analysis apparatus comprising:
a flow cell which includes a flow passage for a liquid containing a tangible component;
a camera configured to pick up images of the liquid flowing through the flow passage;
an adjuster configured to adjust a relative position of the flow cell with respect to the camera in relation to an optical axis direction of the camera and/or a direction in which the liquid flows through the flow passage; and
a controller configured to judge focusing states of pieces of the tangible component in a cutout image obtained by cutting out an image including the tangible component from a plurality of images of the liquid picked up by the camera at a plurality of positions at which the relative position differs, such that the controller is configured to determine an image pickup position of the flow cell in at least one of the optical axis direction and the direction in which the liquid flows, on the basis of a number of the pieces of the tangible component judged to be in the focusing states,
wherein the controller is further configured to generate the cutout image which is an image including one piece of the tangible component and a background existing therearound included in the image picked up by the camera, a blur image which is obtained by applying a blur process to the cutout image, a mask image which is obtained by applying a mask process to the background included in the cutout image, and a differential image which is based on differences between pixel values of the cutout image and pixel values of the blur image, and the controller is further configured to judge that the tangible component included in the cutout image is in the focusing state if a difference, which is provided between a standard deviation of pixel values of pixels existing in a range in which masking is not caused and a standard deviation of pixel values of pixels existing in a range in which masking is caused in relation to the differential image masked with the mask image, is not less than a threshold value.

5. The analysis apparatus according to claim 4, further comprising a light source for image pickup which emits light a plurality of times within an exposure time for one time of exposure performed by the camera.

6. The analysis apparatus according to claim 4, wherein
the flow passage includes a merging portion where a passage through which the test specimen containing the tangible component flows and a passage through which a sheath liquid flows merge, and a tapered portion formed downstream of the merging portion;
the test specimen and the sheath liquid which flowed through the tapered portion flow through the flow passage in a laminar flow without being mixed; and
the camera picks up images of the liquid flowing downstream from the tapered portion.

7. A focusing method comprising:
picking up images of a liquid flowing through a flow passage of a flow cell at a plurality of positions in an optical axis direction of an camera;
cutting out images including pieces of the tangible component in the images picked up at the plurality of positions in the optical axis direction, and judging focusing states of a cutout image;
detecting a focusing point position in the optical axis direction on the basis of a number of the pieces of the tangible component of the cutout image judged to be in the focusing states at the plurality of positions in the optical axis direction;
picking up images at a plurality of positions in a direction in which the liquid flows through the flow passage;
judging focusing states of the cutout image including pieces of the tangible component existing in the images picked up at the plurality of positions in which the liquid flows;
detecting a focusing point position in the direction in which the liquid flows, on the basis of a number of the pieces of the tangible component of the cutout image judged to be in the focusing states at the plurality of positions in the direction in which the liquid flows;
generating the cutout image which is an image including one piece of the tangible component and a background existing therearound, from the picked-up image;
generating a blur image in which a blur process is applied to the cutout image;
generating a mask image in which a mask process is applied to the background included in the cutout image;
generating a differential image which is based on differences between pixel values of the cutout image and pixel values of the blur image; and
judging that the tangible component included in the cutout image is in the focusing state if a number of pixels each having a pixel value of not less than a threshold value existing in a range in which masking is not caused when the differential image is masked with the mask image is not less than a predetermined number.

8. The focusing method according to claim 7, wherein
in the picking up images:
the test specimen including pieces of the tangible component and a sheath liquid flow through the flow passage in a laminar flow without being mixed; and
picking up images of the test specimen is performed.

9. A focusing method comprising:

picking up images of a liquid flowing through a flow passage of a flow cell at a plurality of positions in an optical axis direction of an camera;

cutting out images including pieces of the tangible component in the images picked up at the plurality of positions in the optical axis direction, and judging focusing states of a cutout image;

detecting a focusing point position in the optical axis direction on the basis of a number of the pieces of the tangible component of the cutout image judged to be in the focusing states at the plurality of positions in the optical axis direction;

picking up images at a plurality of positions in a direction in which the liquid flows through the flow passage;

judging focusing states of the cutout image including pieces of the tangible component existing in the images picked up at the plurality of positions in which the liquid flows;

detecting a focusing point position in the direction in which the liquid flows, on the basis of a number of the pieces of the tangible component of the cutout image judged to be in the focusing states at the plurality of positions in the direction in which the liquid flows;

generating the cutout image which is an image including one piece of the tangible component and a background existing therearound included in the picked-up image;

generating a blur image in which a blur process is applied to the cutout image;

generating a mask image in which a mask process is applied to the background included in the cutout image;

generating a differential image which is based on differences between pixel values of the cutout image and pixel values of the blur image; and judging that the tangible component included in the cutout image is in the focusing state if a difference, which is provided between a standard deviation of pixel values of pixels existing in a range in which masking is not caused and a standard deviation of pixel values of pixels existing in a range in which masking is caused in relation to the differential image masked with the mask image, is not less than a threshold value.

10. The focusing method according to claim 9, wherein in the picking up images:

the test specimen including pieces of the tangible component and a sheath liquid flow through the flow passage in a laminar flow without being mixed; and picking up images of the test specimen is performed.

\* \* \* \* \*